(12) United States Patent
Delman et al.

(10) Patent No.: US 11,918,232 B2
(45) Date of Patent: Mar. 5, 2024

(54) MEDICAL DRILL AND IMPLANT DEVICE AND METHOD OF USING THE SAME

(71) Applicant: Peninsula Surgical Solutions, LLC, San Pedro, CA (US)

(72) Inventors: Allan Michael Delman, Rolling Hills, CA (US); Connor Mitchell Delman, Sacramento, CA (US); Jos Cocquyt, Hood River, OR (US); Lon Glazner, Chico, CA (US)

(73) Assignee: Peninsula Surgical Solutions, LLC

( * ) Notice: Subject to any disclaimer, the term of this patent is extended or adjusted under 35 U.S.C. 154(b) by 0 days.

(21) Appl. No.: 18/459,264

(22) Filed: Aug. 31, 2023

(65) Prior Publication Data

US 2023/0404600 A1 Dec. 21, 2023

Related U.S. Application Data

(62) Division of application No. 18/183,503, filed on Mar. 14, 2023, now Pat. No. 11,779,348.

(60) Provisional application No. 63/320,523, filed on Mar. 16, 2022.

(51) Int. Cl.
*A61B 17/16* (2006.01)
*A61B 17/00* (2006.01)
*A61B 17/56* (2006.01)

(52) U.S. Cl.
CPC ...... *A61B 17/1617* (2013.01); *A61B 17/1624* (2013.01); *A61B 2017/00464* (2013.01); *A61B 2017/00473* (2013.01); *A61B 2017/564* (2013.01)

(58) Field of Classification Search
CPC ............ A61B 17/1617; A61B 17/1624; A61B 2017/00464; A61B 2017/00473; A61B 2017/564
See application file for complete search history.

(56) References Cited

U.S. PATENT DOCUMENTS

| | | | | |
|---|---|---|---|---|
| 2,679,770 A | * | 6/1954 | Carter | B25F 3/00 408/714 |
| 3,300,856 A | * | 1/1967 | Daugherty | B23Q 3/15773 483/63 |
| 3,421,351 A | | 1/1969 | Doran et al. | |
| 3,570,606 A | | 3/1971 | Guritz | |
| 4,358,888 A | | 11/1982 | Zankl et al. | |
| 4,404,727 A | | 9/1983 | Zankl | |
| 4,976,175 A | * | 12/1990 | Hung | B25F 1/04 81/439 |
| 5,065,498 A | * | 11/1991 | McKenzie | B23Q 3/15706 483/57 |
| 5,597,275 A | * | 1/1997 | Hogan | B25B 23/0035 408/239 R |
| 5,833,404 A | * | 11/1998 | Johnson | B23Q 16/003 408/130 |

(Continued)

FOREIGN PATENT DOCUMENTS

CN 107997817 A 5/2018

*Primary Examiner* — Zade Coley
(74) *Attorney, Agent, or Firm* — Seed IP Law Group LLP

(57) ABSTRACT

The present disclosure is directed to a drill and implant device and method for using the same. The device is configured to drill a hole into an object, such as a bone; stop once a desired depth has been reached; and subsequently insert an implant, such as a screw or pin, into the hole. The device drills the hole and inserts the implant under its own power. The device may perform desired actions automatically or manually.

20 Claims, 13 Drawing Sheets

(56) References Cited

U.S. PATENT DOCUMENTS

| | | | | |
|---|---|---|---|---|
| 6,715,969 B2* | 4/2004 | Eriksen | ............... | B23B 45/003 |
| | | | | 408/239 R |
| 6,928,908 B1* | 8/2005 | Yu | ...................... | B25G 1/085 |
| | | | | 81/439 |
| 7,395,876 B1* | 7/2008 | Walker | ................... | B25B 21/00 |
| | | | | 173/217 |
| 8,413,549 B2* | 4/2013 | Chen | ...................... | B25B 15/04 |
| | | | | 81/439 |
| 8,894,654 B2* | 11/2014 | Anderson | ............ | B25B 21/002 |
| | | | | 173/176 |
| 9,421,681 B2* | 8/2016 | Zhang | ................... | B25F 5/029 |
| 9,662,716 B2* | 5/2017 | Liu | ..................... | B23B 49/008 |
| 9,833,884 B2* | 12/2017 | Andriolo | .................. | B25F 1/04 |
| 9,925,599 B2* | 3/2018 | Liu | ...................... | B23B 45/008 |
| 11,337,743 B1* | 5/2022 | Nasr | ..................... | A61B 17/865 |
| 2009/0245956 A1 | 10/2009 | Apkarian et al. | | |
| 2009/0326537 A1* | 12/2009 | Anderson | ............ | A61B 17/17 |
| | | | | 606/80 |
| 2010/0331852 A1 | 12/2010 | Neubardt | | |
| 2011/0245833 A1* | 10/2011 | Anderson | ............ | B25B 21/002 |
| | | | | 606/80 |
| 2013/0032368 A1* | 2/2013 | Zhang | ................... | B25F 5/029 |
| | | | | 173/217 |
| 2013/0244845 A1* | 9/2013 | Nagy | ................. | F21V 33/0084 |
| | | | | 483/58 |
| 2013/0245629 A1* | 9/2013 | Xie | .................... | A61B 17/1624 |
| | | | | 606/80 |
| 2016/0067006 A1 | 3/2016 | Steinberg | | |
| 2017/0245868 A1 | 8/2017 | McGinley et al. | | |
| 2018/0000526 A1* | 1/2018 | O'Neil | .................. | A61B 50/20 |
| 2018/0325528 A1* | 11/2018 | Windolf | ............ | A61B 17/1622 |

\* cited by examiner

MEDICAL DRILL AND IMPLANT DEVICE AND METHOD OF USING THE SAME

BACKGROUND

Technical Field

The present disclosure is directed to a medical device and method for using the same.

Description of the Related Art

Orthopedic surgeons treat musculoskeletal system ailments, such as injuries to bones, joints, and ligaments. This may require the insertion of a fastener or implant, such as a screw or pin, into bone. Generally, the implant is inserted into the bone by drilling a hole into the bone with a drill bit, removing the drill bit from the hole, measuring the depth of the hole with a depth gauge, inserting the implant into the hole with a screwdriver, and repeating this process for each implant. This process has several drawbacks.

One drawback is that the orthopedic surgeon uses physical force to push the drill while driving the drill bit into the bone. Similarly, manual force is used to withdraw the drill bit and to insert the screw into the hole with a screwdriver. These actions, which are often done repetitively, are fatiguing.

Furthermore, drilling a hole in bone often requires substantial force and may result in the inadvertent passage of the drill too far, potentially injuring the patient by penetrating the soft tissue. In addition, the surgeon may mistakenly insert the screw into the hole at the wrong angle and/or trajectory impairing the strength or effectiveness of the implant.

In addition, current drills do not detect when the far bone cortex has been penetrated or the length between the near and far bone cortex. Instead, depth gauges are typically used.

Unfortunately, it is often difficult for the surgeon to obtain an accurate measurement of depth using the depth gauge because it requires tactile feedback, which can be demanding in the clinical setting. If the depth measurement is inaccurate, the surgeon may insert a screw of the wrong length, which should then be removed and discarded, resulting in wasted hardware and increased costs. In addition, if the depth measurement is inaccurate or technically difficult, verification may require repeated radiographs, which is time consuming. As a result, patients are subjected to longer anesthesia times and there is greater radiation exposure to the patient, the surgeon, and the ancillary medical staff.

BRIEF SUMMARY

The present disclosure is directed to a drill and implant device and method for using the same. The device is configured to automatically drill a hole into an object, such as a bone, stop once a desired depth has been reached, retract automatically, and subsequently insert an implant into the hole. The device drills the hole and inserts the implant without physical intervention on part of a user. More specifically, in contrast to traditional drills and screwdrivers, the user does not apply a physical force to the device to drill the hole or insert the implant. Rather, the device drills the hole and inserts the implant under its own power. In addition, the user does not move the device when switching between drilling the hole to inserting the implant. Instead, the device may remain stationary during both the drilling of the hole and the insertion of the implant. Accordingly, surgical efficiency and accuracy are improved, and radiation exposure is reduced.

BRIEF DESCRIPTION OF THE SEVERAL VIEWS OF THE DRAWINGS

In the drawings, identical reference numbers identify similar features or elements. The size and relative positions of features in the drawings are not necessarily drawn to scale.

DETAILED DESCRIPTION

In the following description, certain specific details are set forth in order to provide a thorough understanding of various aspects of the disclosed subject matter. However, the disclosed subject matter may be practiced without these specific details. In some instances, well-known structures and methods of using electrical components and devices, such as drills, screwdrivers, and sensors, have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

The present disclosure is directed to a drill and implant device and method for using the same.

Figure 1:
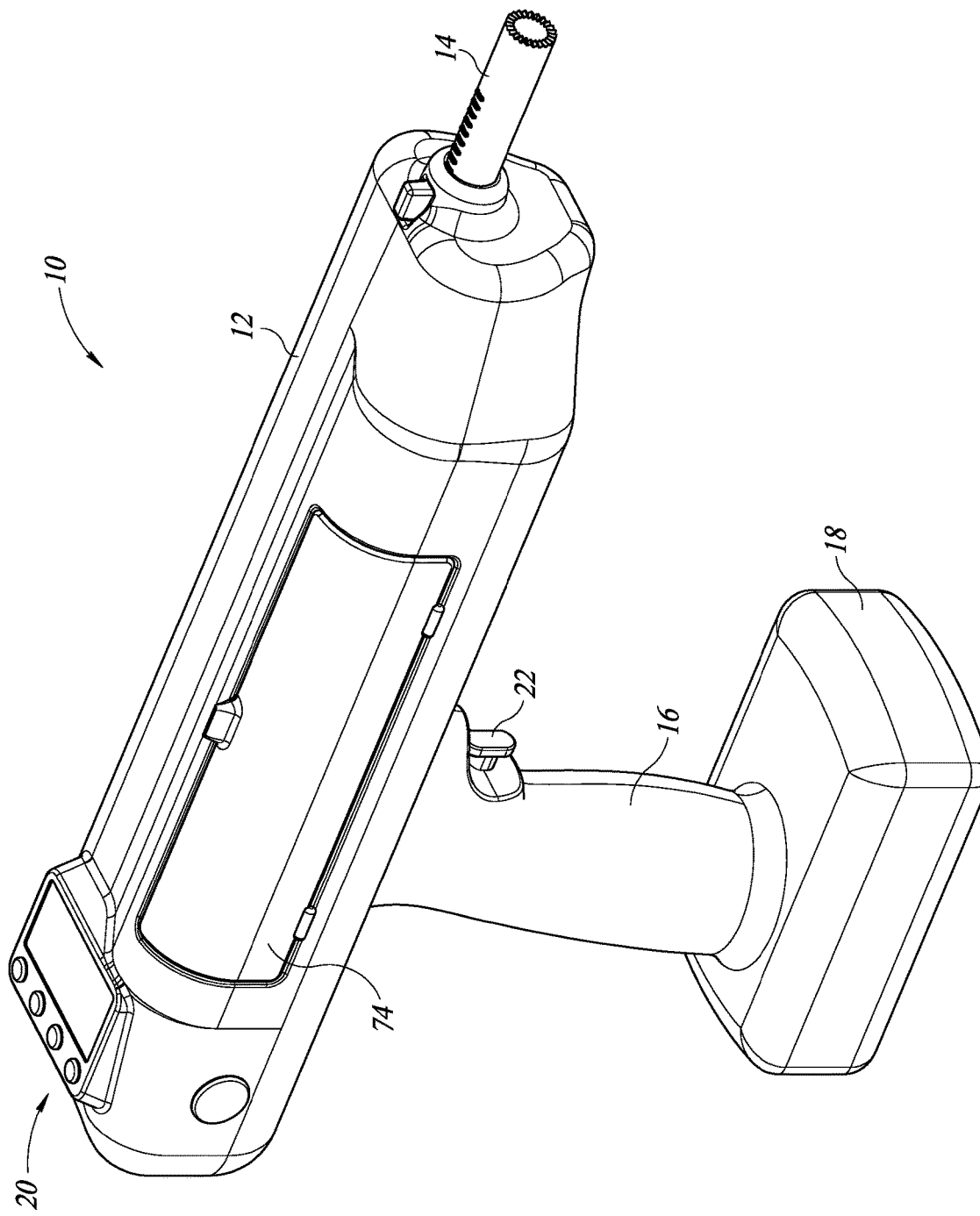
FIG. 1 is an angled view of a drill and implant device according to an embodiment disclosed herein.

FIG. 1 is an angled view of a drill and implant device 10 according to an embodiment disclosed herein. The device 10 includes a body 12, a barrel 14, a handle 16, a base 18, a user interface 20, and a trigger 22.

The body 12 is a housing that contains internal components of the device 10, such as a tool changer and a delivery device. The body 12 includes a door 74 that opens to expose the internal components of the device 10. The internal components will be discussed in further detail below.

The barrel 14 is coupled to the housing at a front end of the body 12, which is placed at a target location (e.g., femur, knee, spine, tibia, etc.). Various drill bits, screws, and pins exit out of the body 12 from the barrel 14. In FIG. 1, the barrel 14 has a cylindrical shape. Other shapes are also possible. The barrel 14 is sometimes referred to as a cannula.

The handle 16 is coupled to the body 12. The handle 16 allows a user to hold and handle the device 10 with a single hand or with two hands. The handle 16, in addition to the body 12, may contain internal components of the device 10, such as a processor and various electrical components.

The body 12, the barrel 14, and the handle 16 are made of one or more rigid materials, such as metal and plastic.

The base 18 is coupled to the handle 16, and supports the device 10. The base 18 may also contain internal components of the device 10, such as a processor and various electrical components. In one embodiment, the base 18 includes a power source that provides electrical power for the various components of the device 10.

The user interface 20 is positioned on the body 12. In one embodiment, as shown in FIG. 1, the user interface 20 and the barrel 14 are positioned at opposite sides of the body 12. The user interface may be positioned at other locations, such as on the handle 16 or the base 18. The user interface 20 includes a display and a plurality of user inputs.

The display of the user interface 20 displays information to a user. The information includes various types of data and parameters related to the device 10 and processes performed by the device 10. For example, the display displays a size and type of tool (e.g., drill bit, screwdriver bit) and implant (e.g., screw or pin) currently loaded in the device 10, measurements generated by the device 10 (e.g., depth measurement of a current hole being drilled), and parameters of the device 10 (e.g., current torque level, current drilling or screwing speed, current power level). The information also includes various modes, such as an automatic mode or manual mode of the device 10. As discussed in further detail below, the device 10 may be operated manually by a user or automatically by the processor of the device 10. The display may be any type of display, such as a digital display, light emitting diode (LED) display, organic light emitting diode (OLED) display, etc. The display may also be located at a remote location from the device 10, and communicate with remaining components of the device 10 wirelessly though, for example, Wi-Fi and Bluetooth.

Figure 2:
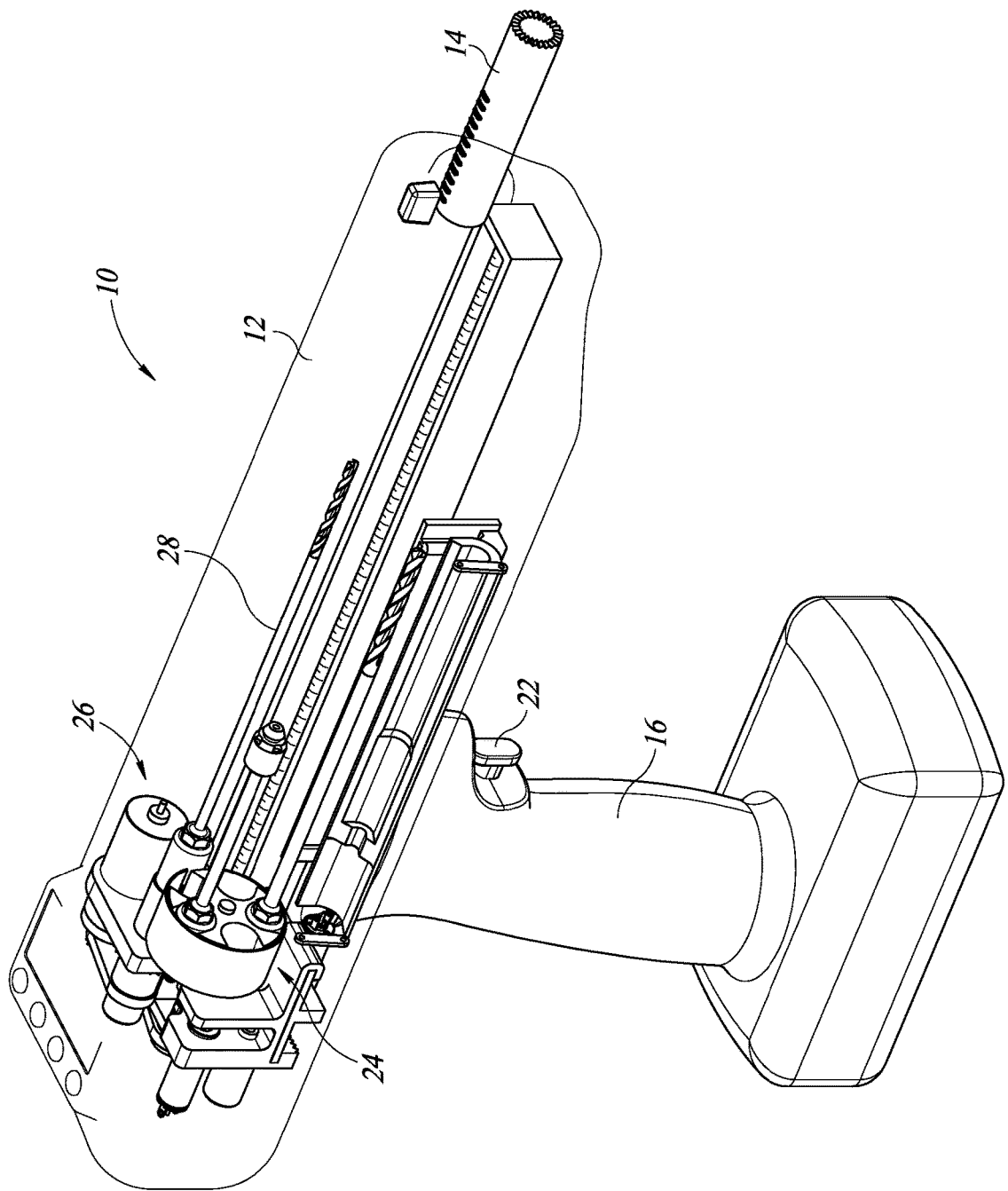
FIG. 2 is an angled internal view of a drill and implant device according to an embodiment disclosed herein.

The user inputs of the user interface 20 are used by a user to input information and instructions into the device 10. For example, the user inputs may be used to start a drill and implantation process, set a size and type of tool (e.g., drill bit, screwdriver bit) and implant (e.g., screw or pin) currently loaded in the device 10, set parameters (e.g., maximum torque level, drilling speed, and screwing speed) of the device 10, and set a target depth of a hole drilled by the device 10. The user inputs may be any type of input device, such as a keyboard, a touchscreen, buttons, a dial, etc. In one embodiment, as shown in FIG. 2, the user inputs include a plurality of buttons. Instead of the user inputs, the user interface 20 may also be controlled remotely though, for example, Wi-Fi and Bluetooth.

The trigger 22 is positioned on the handle 16. In a manual mode of the device 10 in which the device operates similar to that of a standard drill, the trigger 22 is used to start and stop drilling and implantation processes. For example, a user may start drilling by squeezing the trigger 22, and stop drilling by releasing the trigger 22. In an automatic mode in which a drilling and implantation processes may be performed without user intervention, the trigger 22 may not be used or used to initiate the process.

FIG. 2 is an angled internal view of the device 10 according to an embodiment disclosed herein. A portion of the body 12 is removed to show the internals of the device 10. The device 10 includes a tool changer 24 and a delivery device 26. The tool changer 24 and the delivery device 26 are coupled to each other, and/or coupled to a frame or the body 12 of the device 10.

The tool changer 24 is positioned in the body 12. The tool changer 24 loads and unloads tools, such as drill bits, screwdriver bits, screws, pins, and anchors, from the delivery device 26. The components and operation of the tool changer 24 will be discussed in further detail below.

The delivery device 26 is positioned in the body 12. The delivery device 26 is also positioned lateral to the tool changer 24. Other positions are also possible. The delivery device 26 is loaded or mounted with tools by the tool changer 24, and operates with the loaded tool. Namely, the delivery device 26 concurrently moves forward towards the barrel 14 and rotates the loaded tool. In a case where the delivery device 26 is mounted with a drill bit, the delivery device 26 concurrently moves forward and rotates the drill bit to drill into a target location (e.g., femur, knee, spine, tibia, etc.). In a case where the delivery device 26 is mounted with a screwdriver bit, the delivery device 26 concurrently moves forward and rotates the screwdriver bit to screw in a screw or pin into a target location.

Figure 3:
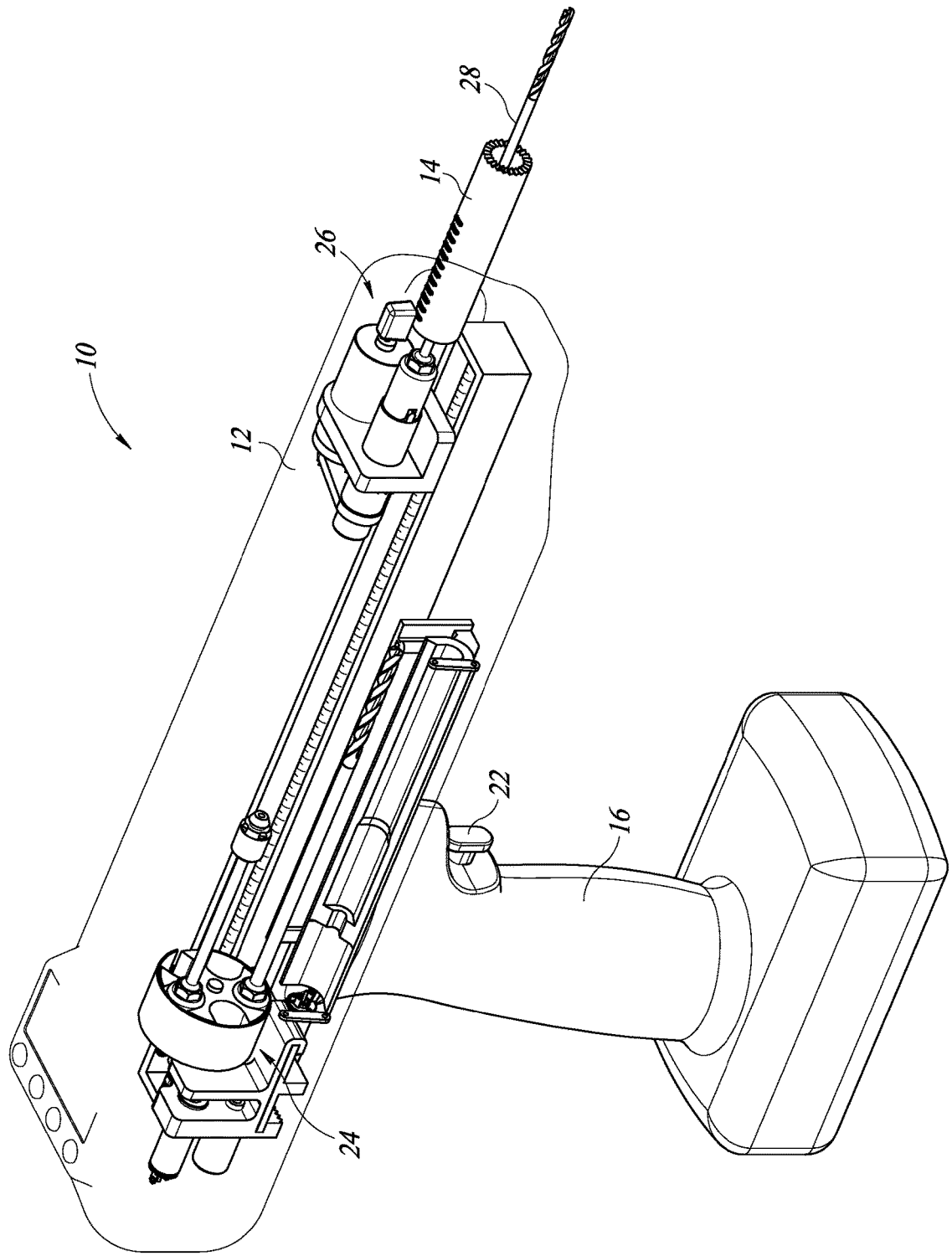
FIG. 3 is the angled internal view with a delivery device in a forward position according to an embodiment disclosed herein.

As the delivery device 26 moves forward, the tool extends out of the body 12 and exits through the barrel 14. For example, FIG. 3 is the angled internal view with the delivery device 26 in a forward position according to an embodiment disclosed herein. A portion of the body 12 is removed to show the internals of the device 10. As compared to FIG. 2, a drill bit 28 mounted on the delivery device 26 protrudes from the barrel 14. As such, the drill bit 28 may enter a target location. The components and operation of the delivery device 26 will be discussed in further detail below.

Figure 4:
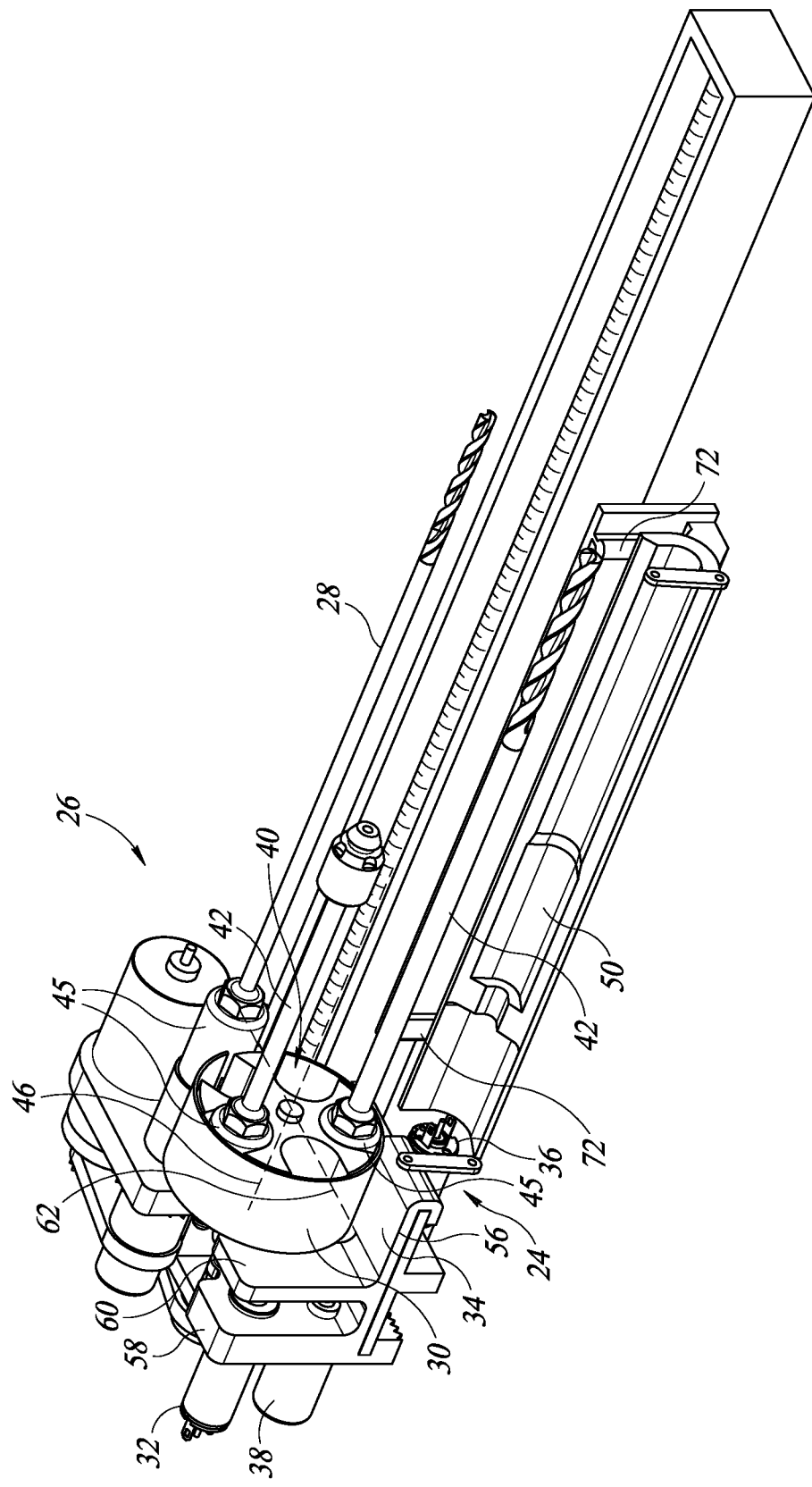
FIG. 4 is a first angled view of a tool changer and a delivery device of a drill and implant device according to an embodiment disclosed herein.

The tool changer 24 is now discussed in further detail. FIG. 4 is a first angled view of the tool changer 24 and the delivery device 26 of the device 10 according to an embodiment disclosed herein. In the first angled view, the tool changer 24 is positioned closer to the reader than the delivery device 26. The remaining components of the device 10 are also removed in FIG. 4.

Figure 5:
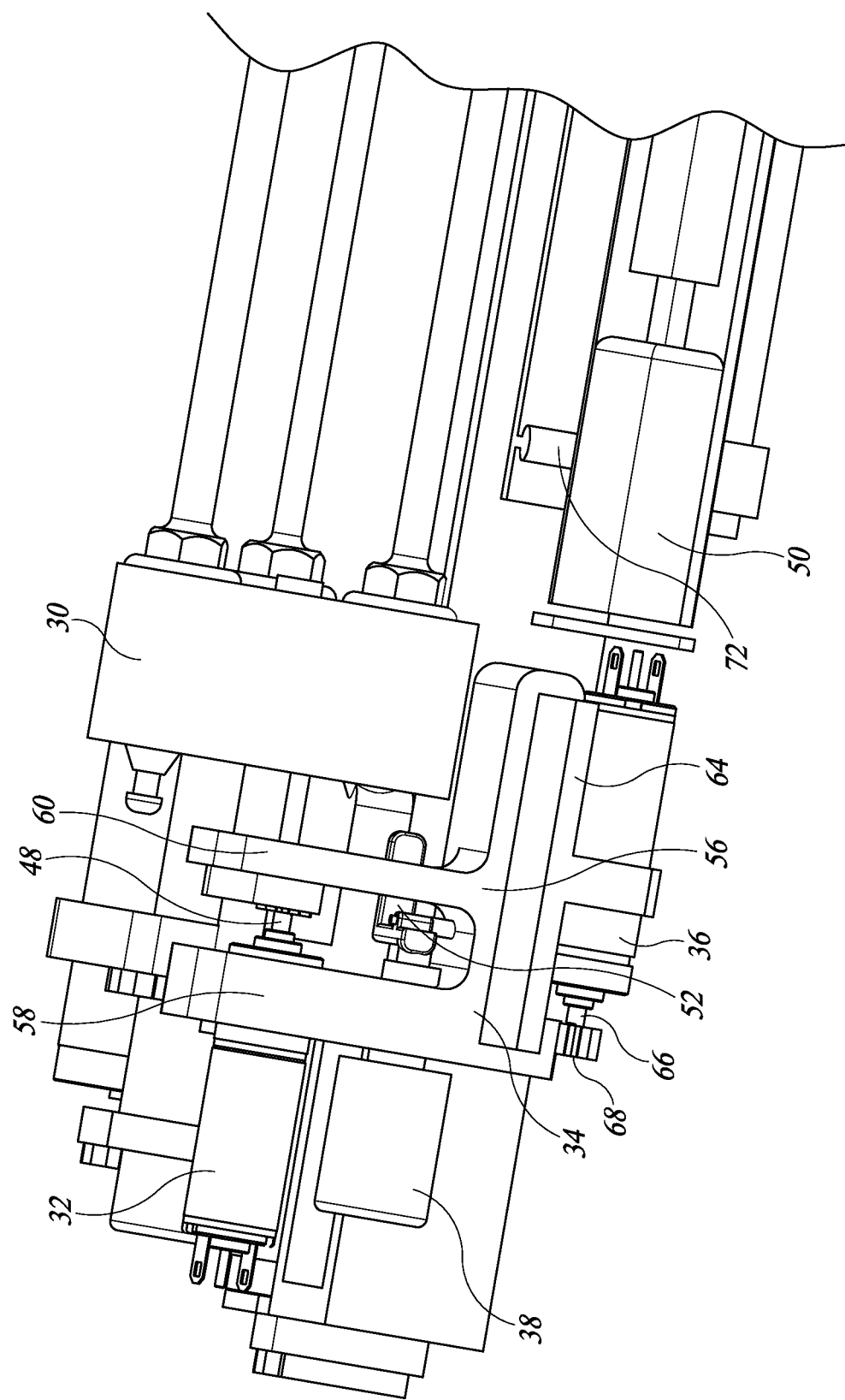
FIG. 5 is a first enlarged angled view of a tool changer according to an embodiment disclosed herein.
Figure 6:
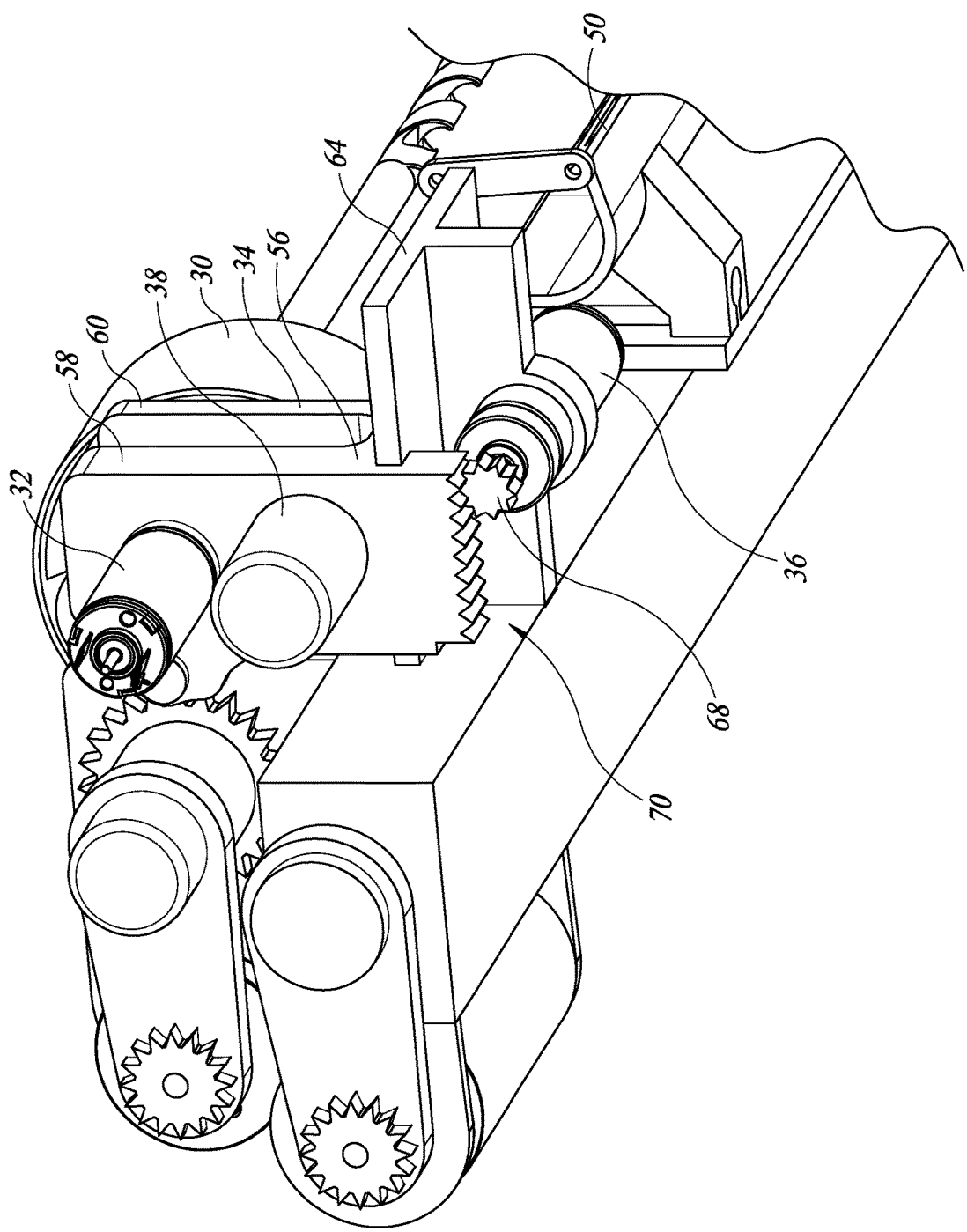
FIG. 6 is a second enlarged angled view of a tool changer according to an embodiment disclosed herein.
Figure 7:
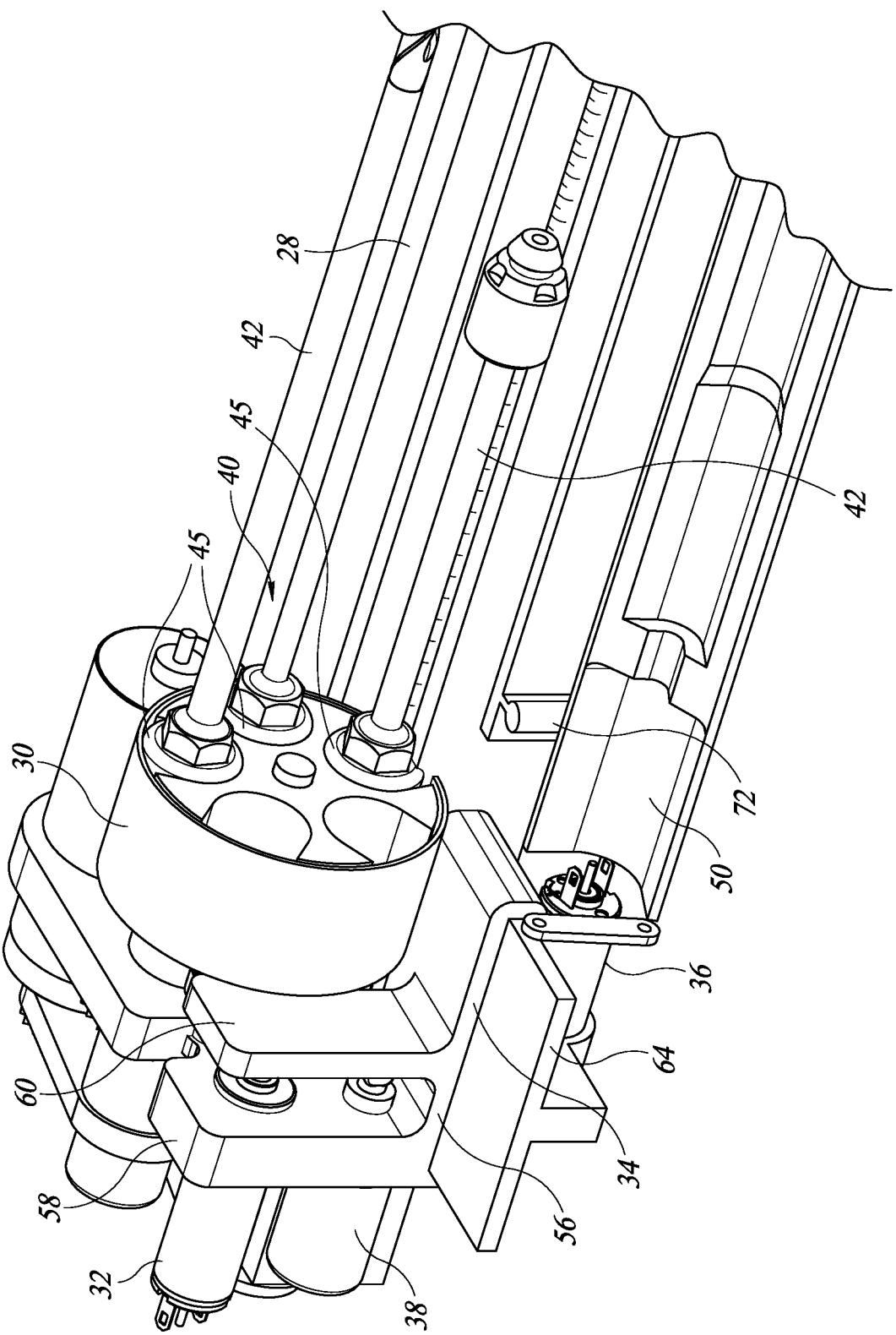
FIG. 7 is a third enlarged angled view of a tool changer according to an embodiment disclosed herein.

FIG. 5 is a first enlarged angled view of the tool changer 24 according to an embodiment disclosed herein, FIG. 6 is a second enlarged angled view of the tool changer 24 according to an embodiment disclosed herein, and FIG. 7 is a third enlarged angled view of the tool changer 24 according to an embodiment disclosed herein. It is beneficial to review FIGS. 4, 5, 6, and 7 together. As will be discussed in further detail below, the tool changer 24 is in a loading position in FIG. 4, and a mounting position in FIGS. 5, 6, and 7.

The tool changer 24 includes a drum 30, a drum motor 32, a collet release actuator 38, a table 34, a table motor 36, and a loading tray 50.

The drum 30 is positioned on the table 34. The drum 30 is a housing that includes a plurality of chambers 40 for holding tools, such as drill bits, screwdriver bits, screws, pins, and anchors. For example, as best shown in FIG. 4, drill bits 42 are loaded into respective chambers 40. The remaining chambers 40 are empty. Tools are loaded in the drum 30 by collets 45. Namely, tools, such as the drill bits 42, are inserted into the collets 45, which in turn are inserted in the drum 30. The collets are also configured to be inserted into a mount of the delivery device 26. Collets 45 for fasteners, such as screws and pins, will be discussed in further detail below.

The drum 30 may hold any number of different types and sizes of bits. For example, a flat head screwdriver bit, a Phillips screwdriver bit, a hex screwdriver bit, a brad point drill bit, and a multi-purpose drill bit of different sizes may be loaded into the chambers 40 at the same time.

Different types and sizes of screws and pins may also be loaded into the chambers 40. In one embodiment, the drum 30 holds at least one drill bit, at least one screwdriver bit, and at least one screw or pin.

As best shown in FIG. 4, the drum 30 includes five chambers. The drum 30, however, may include any number of chambers 40. In one embodiment, the drum 30 includes at least two chambers. The drum 30 also has a cylindrical shape. However, other shapes are also possible. For example, the drum 30 may instead have a cross section that is hexagonal, pentagonal, or square shaped.

The drum 30 is configured to rotate around an axis 46 shown in FIG. 4. As will be discussed below, the drum 30 is rotated by the drum motor 32. By rotating around the axis 46, the drum 30 is able to laterally align each of the chambers 40 with a mount of the delivery device 26, one at a time. As will be discussed in further detail below, when a chamber 40 is aligned with the mount of the delivery device 26, a tool in the chamber 40 may be loaded from the chamber 40 and into the mount of the delivery device 26 to be used in a subsequent drill or implantation process.

The drum motor 32 is positioned on the table 34 and is coupled to the drum 30. The drum motor 32 turns the drum 30 to rotate around the axis 46. In one embodiment, as best shown in FIG. 5, the drum motor 32 is coupled to the drum 30 by a gear shaft 48. The gear shaft 48 is coupled to the drum 30 such that the drum 30 rotates as the drum motor 32 rotates the gear shaft 48.

The drum motor 32 may be any type of motor that provides a rotating motion for the drum 30.

The collet release actuator 38 is positioned on the table 34. The collet release actuator 38 unloads a tool, such as the drill bit 28, from the drum 30 to the mount of the delivery device 26. As mentioned above, when a chamber 40 is aligned with the mount of the delivery device 26, a tool in the chamber 40 may be unloaded from the chamber 40 and into the mount of the delivery device 26 to be used in a subsequent drill or implantation process. The tool is transferred from the chamber 40 to the mount by the collet release actuator 38. In one embodiment, as best shown in FIG. 5, an arm 52 of the collet release actuator 38 is actuated to move the tool from the chamber 40 to the mount of the delivery device 26. In one embodiment, each of the collets 45 of the tools employ a retention knob that is grabbed and released by an electronically actuated system that employs a locking ball race that is actuated using collet release actuator 38.

The table 34 provides a support for the other components of the tool changer 24. Namely, the drum 30, the drum motor 32, and the collet release actuator 38 are coupled to the table 34. The table 34 includes a base portion 56, a back sidewall 58, a front sidewall 60, and a guide 64.

The base portion 56 extends in a first direction, and the back sidewall 58 and the front sidewall 60 extend from the base portion 56 in a second direction transverse to the first direction. The base portion 56 is coupled to the guide 64 and configured to slide along the guide 64. The drum 30 is attached to a front sidewall 60 of the table 34, and the drum motor 32 and the collet release actuator 38 are attached to a back sidewall 58 of the table 34. The gear shaft 48, which is coupled between the drum motor 32 and the drum 30, extends from the back sidewall 58 and through the front sidewall 60.

The table 34, more specifically the base portion 56, is configured to move along an axis 62 shown in FIG. 4, which is transverse to the axis 46. As will be discussed below, the table 34 is moved along the axis 62 by the table motor 36. The base portion 56 is configured to slide along the axis 62 while coupled to the guide 64. The guide 64 keeps the table 34 along the axis 62. The table 34 is moved along the axis 62 between a loading position shown in FIG. 4, and a mounting position shown in FIGS. 5, 6, and 7.

In the loading position, referring to FIG. 4, the table 34 is moved leftward along the axis 62 such that none of the chambers 40 are aligned in front of the mount of the delivery device 26. As such, none of the tools loaded in the chamber 40 may be mounted on the mount of the delivery device 26 by the collet release actuator 38. As will be discussed below, tools may be loaded from the loading tray 50 into the drum 30 in the loading position.

In the mounting position, referring to FIG. 4, the drum 30 is rotated until a chamber 40 with a selected tool, such as the drill bit 28, is positioned lateral to the mount of the delivery device 26, and the table 34 is moved rightward along the axis 62 such that the chamber 40 is aligned in front of the mount. When the chamber 40 is aligned with the mount of the delivery device 26, the selected tool is loaded from the chamber 40 and into the mount of the delivery device 26 by the collet release actuator 38 to be used in a subsequent drill or implantation process.

The table motor 36 is positioned on the table 34. Namely, the table motor underlies and is coupled to the guide 64. The table motor 36 moves the table 34, more specifically the base portion 56, along the axis 62. In one embodiment, as best shown in FIGS. 5 and 6, the table motor 36 includes a gear shaft 66 and a gear 68, and the back sidewall 58 includes teeth 70. The gear 68 is engaged with the teeth 70 such that the table 34 moves along the axis 62 as the table motor 36 rotates the gear shaft 66 and the gear 68. The table motor 36 may be any type of motor that provides motion for the table 34.

The loading tray 50 provides a support for tools being loaded into the drum 30, and is used to ensure that a tool being loaded into the drum 30 is properly aligned with one of the chambers 40.

As the door 74 of the body 12 is being closed, the loading tray 50 moves downward along rails 72 until the loading tray 50 is unaligned with (e.g., positioned below) the chamber 40. The position of the loading tray 50 shown in FIGS. 4, 5, 6, and 7 is in the case where the door 74 of the body 12 is closed as shown, for example, in FIG. 1.

Figure 8:
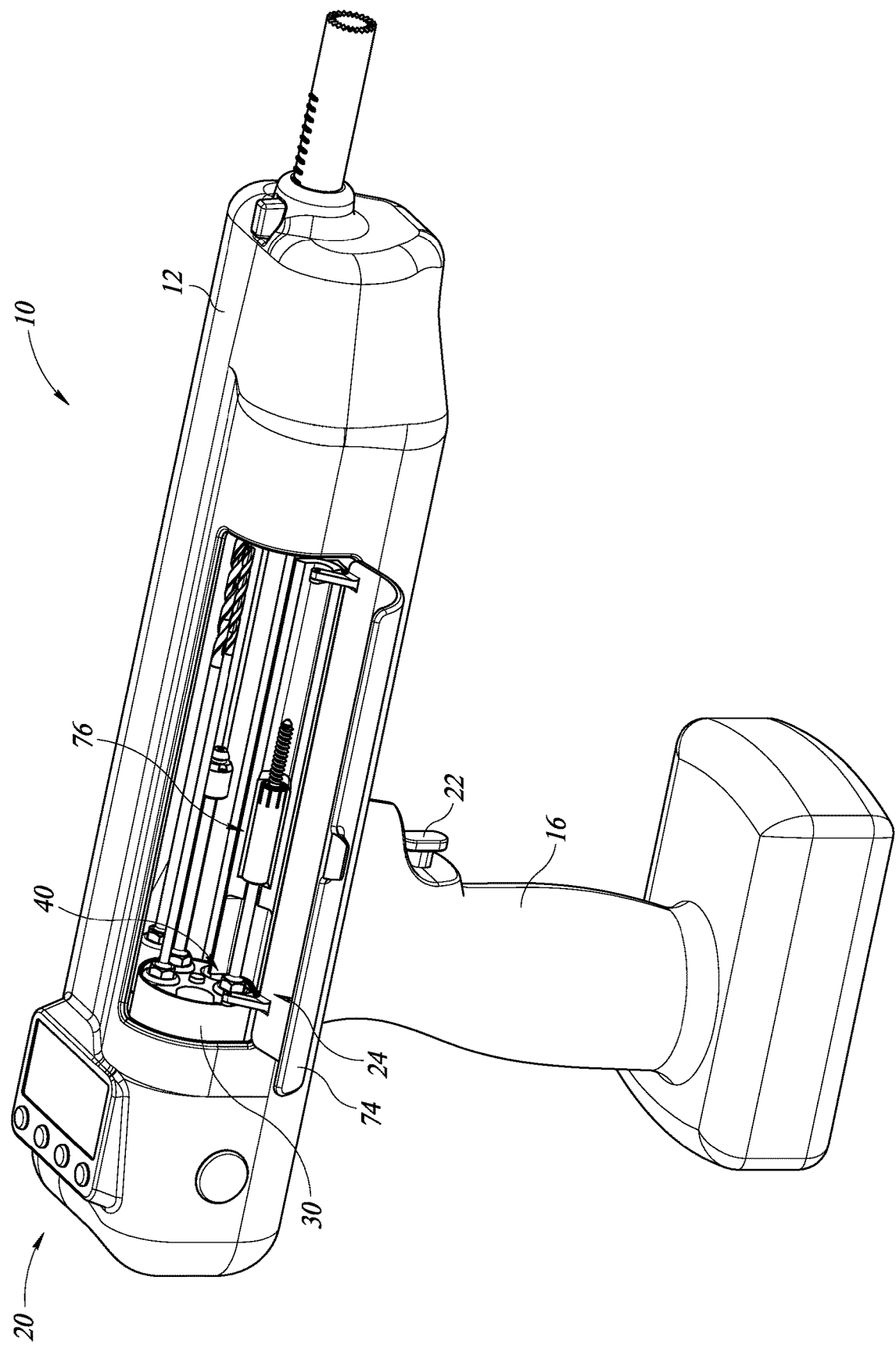
FIG. 8 is an angled view of a drill and implant device with a door opened according to an embodiment disclosed herein.

In contrast, as the door 74 of the body 12 is being opened, the loading tray 50 moves upward along rails 72 until a tool in the loading tray 50 is aligned (e.g., positioned laterally) with a chamber 40. FIG. 8 is an angled view of the device 10 with the door 74 opened according to an embodiment disclosed herein. As shown in FIG. 8, the loading tray 50 is in a position such that a tool in the loading tray 50 is aligned and loaded into one of the chambers 40.

Figure 9:
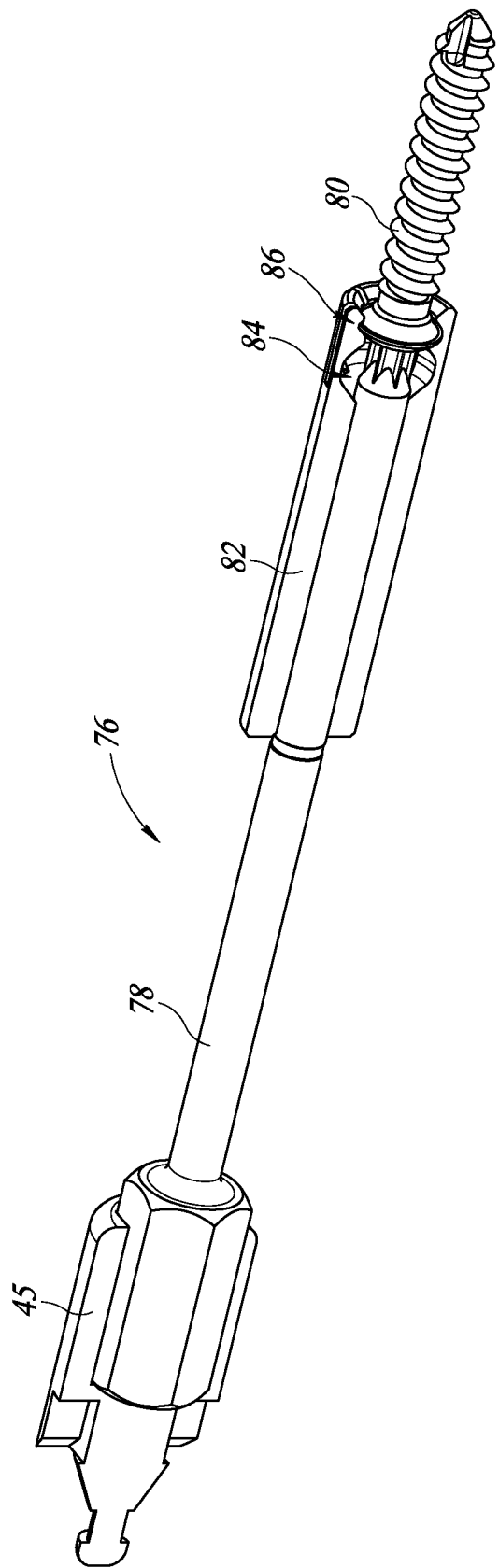
FIG. 9 is a partial cross-sectional view of a screw holder according to an embodiment disclosed herein.

In the example shown in FIG. 8, the tool in the loading tray 50 and the drum 30 is a screw holder 76. The screw holder 76 is used to load fasteners, such as screws, pins, and anchors, into the drum 30. FIG. 9 is a partial cross-sectional view of the screw holder 76 according to an embodiment disclosed herein. The screw holder 76 includes a collet 45, a screwdriver bit 78, a screw 80, and a sleeve 82. Cross sections of the collet 45 and the sleeve 82 are shown in FIG. 9.

The collet 45 holds the screwdriver bit 78, and is inserted into a chamber 40 of the drum 30 as shown in FIG. 8. The sleeve 82 is slid over the tip of the screwdriver bit 78 and the head of the screw 80. The tip of the screwdriver bit 78 is positioned in a first cavity 84 of the sleeve 82, and is spaced away from sidewalls of the first cavity 84. The head of the screw 80 is positioned in a second cavity 86 of the sleeve 82, and contacts sidewalls of the second cavity 86. The sleeve 82 secures the screwdriver bit 78 and the screw 80 to each other such that the tip of the screwdriver bit 78 is positioned in the head of the screw 80 and is able to turn the screw 80 upon rotation. The sleeve 82 is configured to securely hold the screw for insertion into a target location, and release once the screw is fully inserted into the target location. The sleeve 82 is pulled back once the screw 80 is close to its final position in the target location.

It is noted that other types of fasteners that do not have to be screwed in, such as pins, are inserted into collets, which in turn are inserted in the drum and the mount of the delivery device 26 discussed below. These types of fasteners may be inserted and released from the collet by simply being rotated by delivery device 26.

Figure 10:
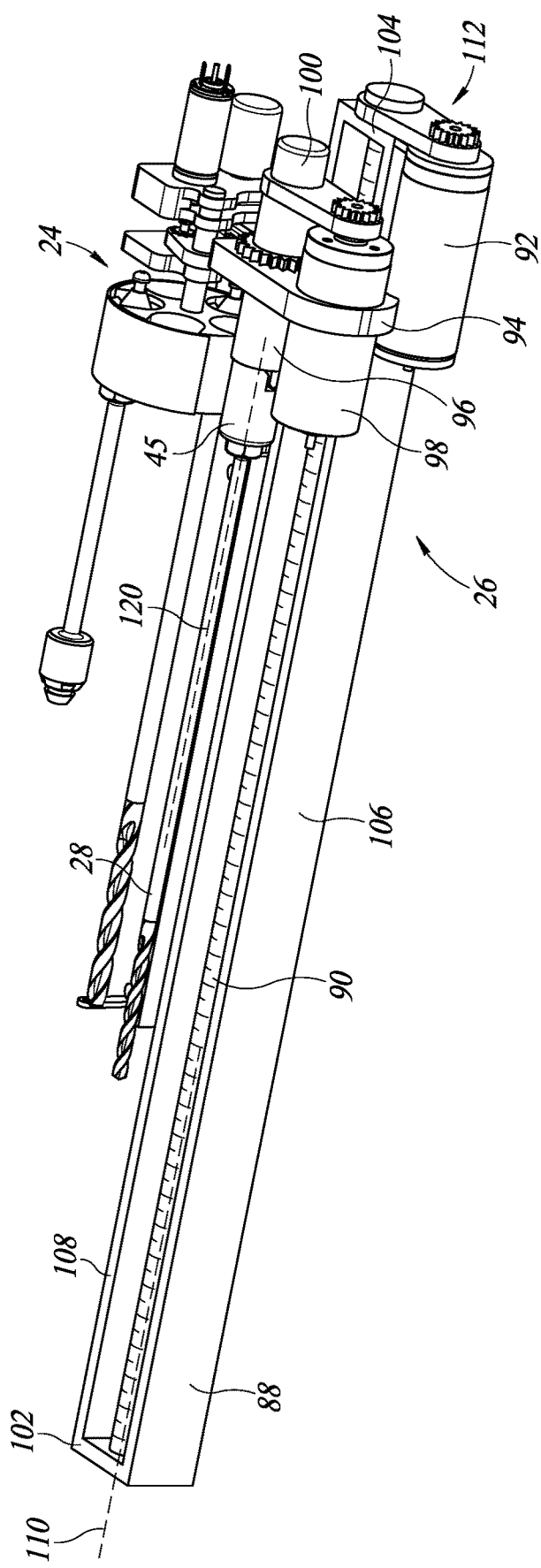
FIG. 10 is a second angled view of a tool changer and a delivery device of a drill and implant device according to an embodiment disclosed herein.
Figure 11:
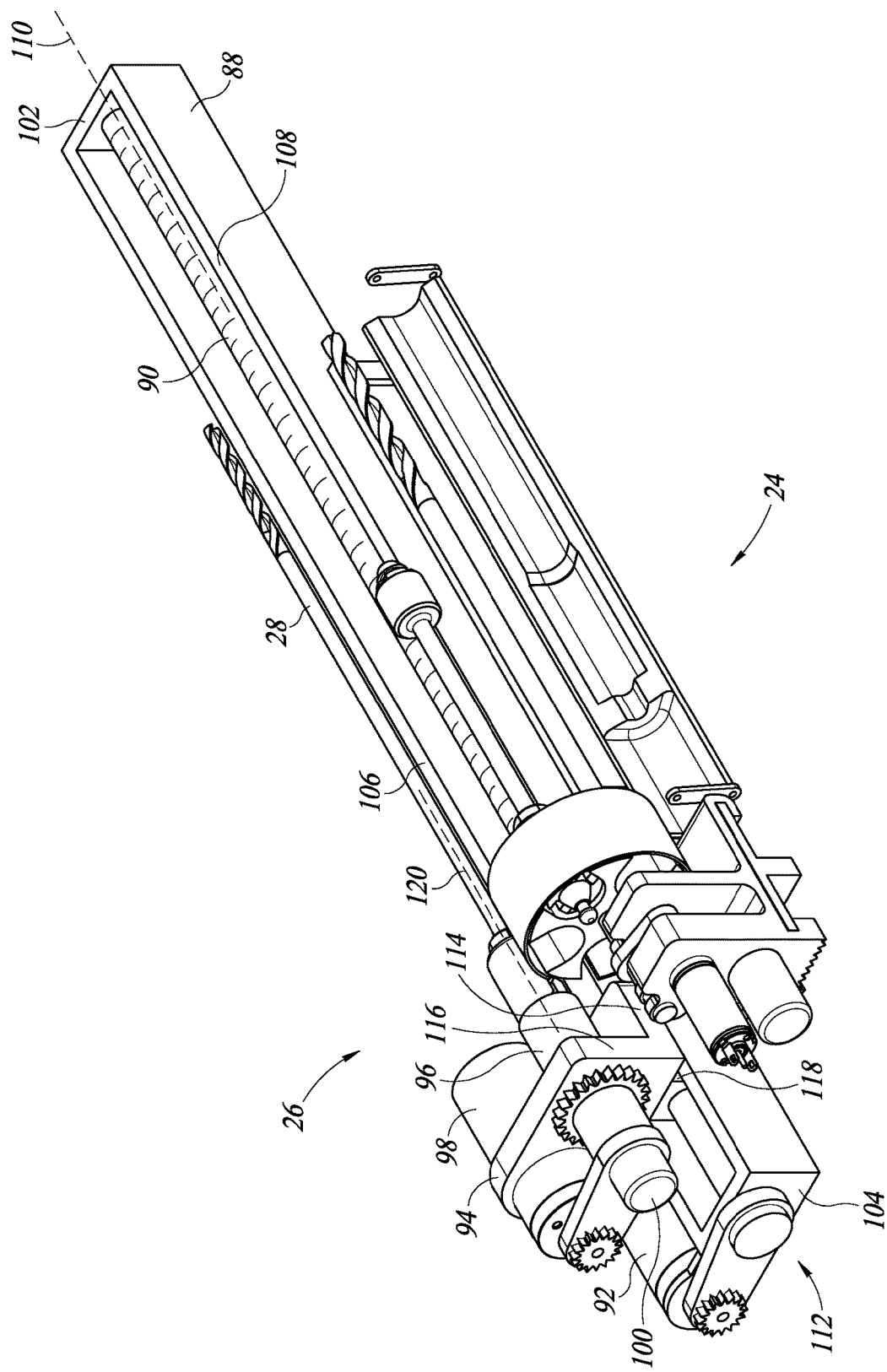
FIG. 11 is a third angled view of a tool changer and a delivery device of a drill and implant device according to an embodiment disclosed herein.

The delivery device 26 is now discussed in further detail. FIG. 10 is a second angled view of the tool changer 24 and the delivery device 26 of the device 10 according to an embodiment disclosed herein, and FIG. 11 is a third angled view of the tool changer 24 and the delivery device 26 of the device 10 according to an embodiment disclosed herein. In the second angled view, the delivery device 26 is positioned closer to the reader than the tool changer 24. The remaining components of the device 10 are also removed in FIGS. 10 and 11. It is beneficial to review FIGS. 10 and 11 together.

The delivery device 26 includes a frame 88, a lead screw 90, a lead screw motor 92, the sled 94, a mount 96, a drive motor 98, and another collet release actuator 100.

The frame 88 provides a support for the other components of the delivery device 26.

Namely, the lead screw 90, the lead screw motor 92, the sled 94, the mount 96, the drive motor 98, and the collet release actuator 100 are coupled to the frame 88. The frame 88 includes a first sidewall 102, a second sidewall 104, a third sidewall 106, and a fourth sidewall 108. In one embodiment, as shown in FIG. 10, the frame 88 is rectangular in shape such that the first and second sidewalls 102, 104 are shorter than the third and fourth sidewalls 106, 108. In one embodiment, the tool changer 24 is also coupled to the frame 88.

The lead screw 90 is coupled to the frame 88 and extends between the first sidewall 102 and the second sidewall 104. The lead screw 90 is a threaded rod having external threads that are mated with a threaded portion 118 of the sled 94. The lead screw 90 is configured to rotate around an axis 110. The axis 110 is parallel to the axis 46 and transverse to the axis 62 discussed above.

The lead screw motor 92 is coupled to the second sidewall 104 of the frame 88 and the lead screw 90. The lead screw motor 92 turns the lead screw 90 to rotate around the axis 110. In one embodiment, as shown in FIG. 10, the lead screw motor 92 is coupled to the lead screw 90 through a series of gears 112. The lead screw motor 92 may be any type of motor that provides a rotating motion for the lead screw 90.

The sled 94 provides a support for the other components of the delivery device 26. Namely, the mount 96, the drive motor 98, and the collet release actuator 100 are coupled to the sled 94. As best shown in FIG. 11, the sled 94 includes a base portion 114, a sidewall 116, and a threaded portion 118.

The base portion 114 extends in a first direction, the sidewall 116 extends from an upper side of the base portion 56 in a second direction transverse to the first direction, and the threaded portion 118 extends from a lower side of the base portion 56 in a third direction transverse to the first direction. The mount 96, the drive motor 98, and the collet release actuator 100 are attached to the sidewall 116.

The threaded portion 118 includes internal threads that are mated with the external threads of the lead screw 90. As a result, the external threads of the lead screw 90 cause the sled 94 to move parallel to axis 110 when the lead screw 90 is rotated by the lead screw motor 92. For example, as shown in FIG. 3, the sled 94, along with the mount 96, the drive motor 98, and the collet release actuator 100, are moved to the forward position upon rotation of the lead screw 90 by the lead screw motor 92. The remaining components, such as the tool changer 24, remain stationary with respect to the handle 16.

The mount 96 is coupled to the sled 94 and moves with the sled 94 along the axis 110. The mount 96 is a bit mount configured to hold or clamp a tool, such as the drill bit 28, to be used in a drill and implantation process. The mount 96 is sometimes referred to as a chuck. The mount 96 rotates around an axis 120. The axis 120 is parallel to the axis 110 and the axis 46, and transverse to the axis 62.

The drive motor 98 is coupled to the sled 94 and moves with the sled 94 along the axis 110. The drive motor 98 turns or rotates the mount 96 around an axis 120. As the drive motor 98 rotates the mount 96, the tool loaded in the mount 96 rotates around an axis 120. For example, as the drive motor 98 rotates the mount 96, the drill bit 28 rotates around the axis 120 to drill. The drive motor 98 may be any type of motor that provides a rotating motion for the mount 96. Although the drive motor 98 and the lead screw motor 92 are shown as separate motors, the functions of the drive motor 98 and the lead screw motor 92 may also be combined and performed by a single motor using, for example, switching couplings and/or gear shifters.

The collet release actuator 100 is coupled to the sled 94 and moves with the sled 94 along the axis 110. In contrast to the collet release actuator 38 of the tool changer 24, the collet release actuator 100 unloads a tool, such as the drill bit 28, from the mount 96 to the drum 30. As discussed above, when a chamber 40 is aligned with the mount 96, a tool in the chamber 40 may be loaded from the chamber 40 and into the mount 96 to be used in a subsequent drill or implantation process. Similarly, a tool in the mount 96 may be unloaded from the mount 96 and back into the chamber 40. The tool is transferred from the mount 96 to the chamber 40 by the collet release actuator 100. In one embodiment, similar to the collet release actuator 38, an arm of the collet release actuator 100 is actuated to move the tool from the mount 96 to the chamber 40.

The device 10 also includes various circuitry, including processors, memory, and electrical components (e.g., capacitors, resistors, etc.) used to control and operate the device 10. For example, the device 10 includes a processor configured to automatically control the components of the device 10 to perform a drill process and an implantation process discussed below. The circuitry may be located anywhere in the device 10, such as in the handle 16, in the base 18, on the tool changer 24, or on the delivery device 26. The processor may be any type of controller, processor, or application specific integrated circuit (ASIC) that executes instructions. The device 10 may also be controlled remotely though, for example, Wi-Fi and Bluetooth.

In one embodiment, the table 34 is removed from the device 10. In this embodiment, the tool changer 24 is positioned on the sled 94, adjacent to the other components of the tool changer 24.

In one embodiment, the tool changer 24 is removed from the device 10. In this embodiment, tools are manually inserted into the mount 96 of the delivery device 26.

Figure 12:
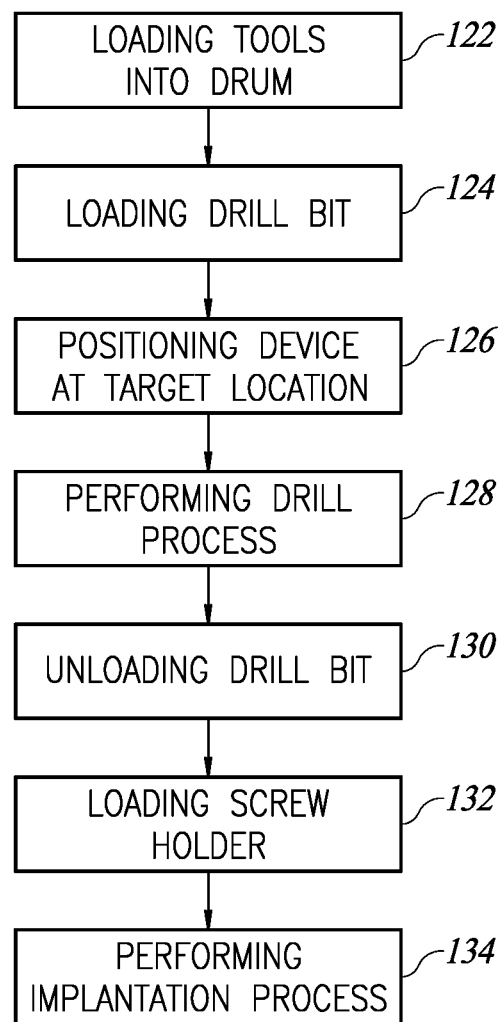
FIG. 12 is a block diagram of a method of operating a drill and implant device according to an embodiment disclosed herein.

FIG. 12 is a block diagram of a method of operating the device 10 according to an embodiment disclosed herein. The method drills a hole into a bone, and subsequently inserts a screw into the hole in the bone. It is noted, however, the method may be used to insert another type of implant, such as a pin, into another type of object. The method may be performed manually by a user of the device 10 or automatically by the processor of the device 10.

In block 122, tools are loaded into the drum 30. Namely, one or more of drill bits, screwdriver bits, awls, and screw holders are placed in the chambers 40 of the drum 30 while the drum 30 is in the loading position.

In block 124, a drill bit is loaded into the mount 96. The drill bit is selected from the drum 30 using the user interface 20, and is inserted into the mount 96, where the drill bit is clamped. A bit is loaded into the mount 96 by rotating the drum 30 until a chamber 40 with the drill bit is positioned lateral to the mount 96. Referring to FIG. 4, the table 34 is then moved rightward along the axis 62 by the table motor 36 until the chamber 40, more specifically the drill bit, is aligned in front of the mount 96 (the mounting position). The collet release actuator 38 then unloads the drill bit from the drum 30 to the mount 96. The table motor 36 returns the table 34 to the loading position.

In block 126, the device 10 is positioned at a target location, such as a bone. The device 10 is positioned such that the barrel 14 is in physical contact with the bone. Once the device 10 is put into position in block 126, the device 10 remains stationary with respect to the handle 16 for the remainder of the method.

In block 128, a drill process is performed. The drill process drills a hole into the bone. During the drill process, the drive motor 98 rotates the mount 96, along with the drill bit, around the axis 120. Concurrently, the sled 94 is moved to the forward position by rotating the lead screw 90 in a first direction with the lead screw motor 92. In one embodiment, speed of the drive motor 98 is reduced once, for example, bone is detected. In one embodiment, the user interface 20 displays a graph of the device's torque output and/or electrical current consumed by the drive motor 98 during the drill process. The torque and electrical current may be used as an estimate of the bone's density, which allows the device 10 to track the drill's process in the bone.

It is noted that the device 10 itself remains stationary with respect to the handle 16 during the drill process in block 128, including the retraction of the drill bit. Further, the user does not apply physical force to push the device 10 to drill the drill bit into the bone. As a result, the user will not suffer from fatigue after drilling several holes.

Once a desired depth of the hole is reached (e.g., a far cortex of a bone), the drill bit is automatically retracted from the bone. The drill bit is retracted by rotating the lead screw 90 in a second direction, opposite to the first direction, with the lead screw motor 92. The drill bit may be retracted manually, or automatically upon the drill bit reaching a target depth in order to minimize the possibility of drilling the hole too deep and injuring the patient by, for example, penetrating soft tissue.

In one embodiment, the drill process is initiated by pulling the trigger 22, but the remaining steps are performed automatically by the processor of the device 10. For example, the drilling process, the retraction of the drill bit, and the subsequent blocks 140, 132, and 132 discussed below are performed automatically by the processor of the device 10 after the trigger 22 is pulled.

Figure 13:
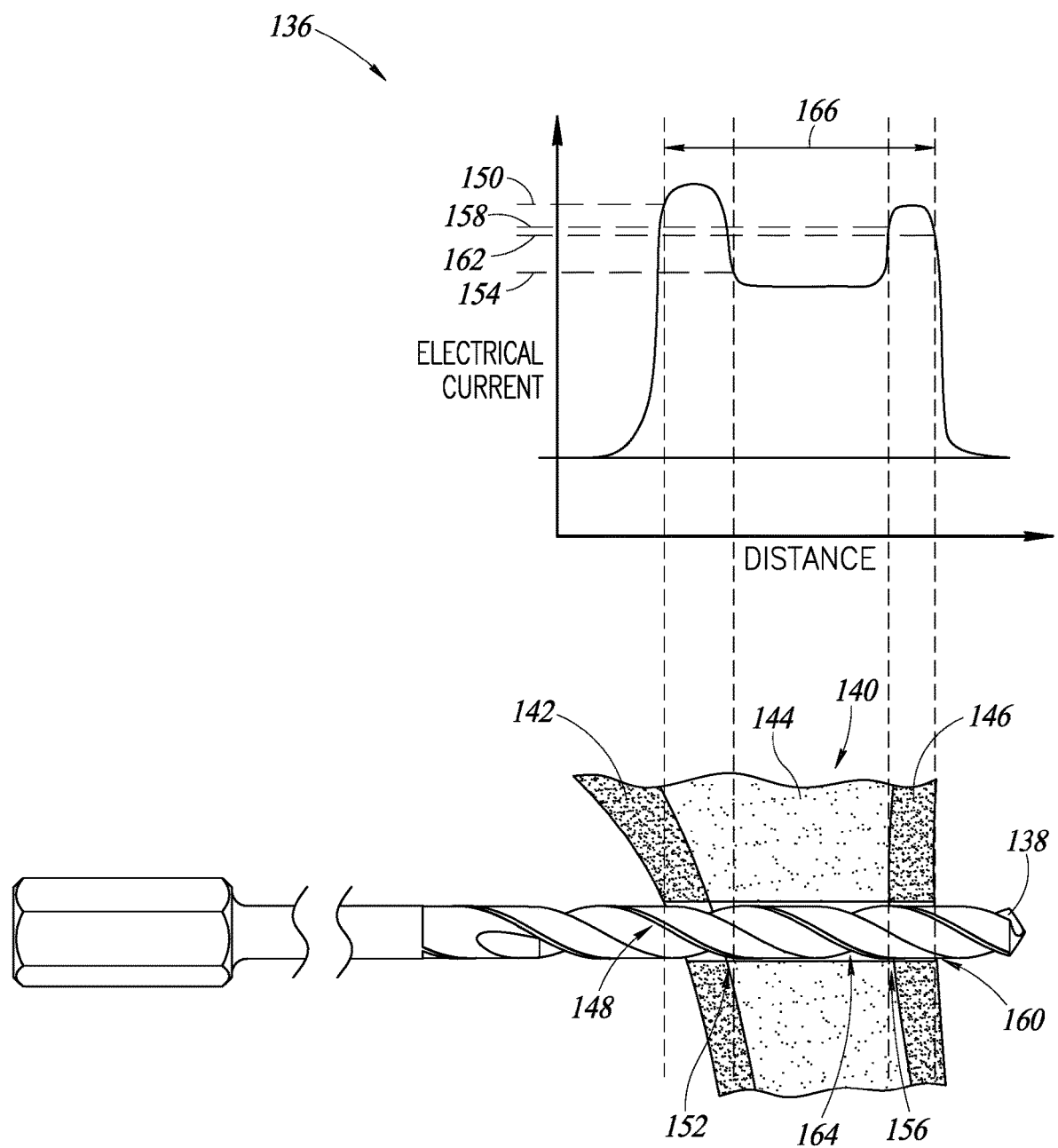
FIG. 13 is a diagram showing distance and electrical current measurements during a drill process according to an embodiment disclosed herein.

An example of how a depth of a hole drilled into a bone is measured in block 128 is shown in FIG. 13. FIG. 13 is a diagram showing distance and electrical current measurements during a drill process according to an embodiment disclosed herein. Graph 136 shows distance measurements versus electrical current measurements, when a drill bit 138 is drilled through a bone 140. The bone 140 includes a near cortex 142, an intramedullary cavity 144, and a far cortex 146.

As can be seen from the graph 136, as the near cortex 142 and the far cortex 146 are harder than the intramedullary cavity 144, electrical current measurements increase as the drill bit 138 goes through the near cortex 142, decreases as the drill bit 138 goes through the intramedullary cavity 144, increases again as the drill bit 138 goes through the far cortex 146, and decreases again as the drill bit 138 exits the far cortex 146 into the soft tissue.

Prior to the drill bit 138 making first physical contact with the near cortex 142 at a position 148, the processor of the device 10 pauses the drill process for a threshold amount of time (e.g., 2,000 milliseconds) to allow electrical current to dissipate from the drive motor 98.

Subsequently, the drive motor 98 begins to drive the drill bit. While the drill bit is driven by the drive motor 98, the processor of the device 10 obtains a first baseline current of the electrical current of the drive motor 98. The processor of the device 10 utilizes, for example, a current sensor or sensing circuitry to measure the electrical current of the drive motor 98. In one embodiment, the first baseline current is an average of the electrical current for a threshold amount of time (e.g., 2,000 milliseconds). As the first baseline current is measured prior to the drill bit 138 making first physical contact with the near cortex 142 at the position 148, the first baseline current represents the electrical current consumed by the drive motor 98 while there is no load on the drill bit (i.e., while nothing is being drilled into).

Once the first baseline current is measured, the drill process as discussed above is initiated. The drive motor 98 rotates the mount 96, along with the drill bit, around the axis 120; and the sled 94 is moved to the forward position by rotating the lead screw 90 in a first direction with the lead screw motor 92.

During the drill process, the processor of the device 10 monitors the electrical current of the drive motor 98, and determines a starting position. The starting position represents the beginning of a hole drilled by the drill bit in the bone 140. In FIG. 13, the starting position is a position 148 where the drill bit makes first physical contact with the near cortex 142. The processor of the device 10 determines the starting position as a position of the drill bit at a time of the electrical current of the drive motor 98 exceeding the first baseline current by a threshold amount. Referring to FIG. 13, the processor of the device 10 determines the electrical current 150 exceeds the first baseline current by the threshold amount, and determines the starting position as the position 148.

After the starting position is determined, the processor of the device 10 continues to monitor the electrical current of the drive motor 98, and determines a near cortex exit position. The near cortex exit position represents the drill bit exiting from the near cortex 142. In FIG. 13, the near cortex exit position is a position 152 where the drill bit exits the near cortex 142. The processor of the device 10 determines the near cortex exit position as a position of the drill bit at a time of the electrical current dropping by a threshold amount. In one embodiment, the processor determines a maximum current as an average of a plurality of previous current measurements, and determines the near cortex exit position as a position of the drill bit at a time of the electrical current drops by a threshold amount from the maximum current. Referring to FIG. 13, the processor of the device 10 determines the electrical current 154 drops by the threshold amount, and determines the near cortex exit position as the position 152.

Next, the processor of the device 10 obtains a second baseline current of the electrical current of the drive motor 98. In one embodiment, the second baseline current is an average of the electrical current for a threshold amount of time (e.g., 2,000 milliseconds). As the second baseline current is taken while the drill bit is in the intramedullary cavity 144, the second baseline current represents the electrical current consumed by the drive motor 98 while the drill bit is drilling through the intramedullary cavity 144.

Once the second baseline current is measured, the processor of the device 10 continues to monitor the electrical current of the drive motor 98, and determines a far cortex starting position. The far cortex starting position represents the drill bit entering the far cortex 146. In FIG. 13, the far cortex starting position is a position 156 where the drill bit enters the far cortex 146. The processor of the device 10 determines the far cortex starting position as a position of the drill bit at a time of the electrical current of the drive motor 98 exceeding the second baseline current by a threshold amount. Referring to FIG. 13, the processor of the device 10 determines the electrical current 158 exceeds the second baseline current by the threshold amount, and determines the far cortex starting position as the position 156.

After the far cortex starting position is determined, the processor of the device 10 continues to monitor the electrical current of the drive motor 98, and determines an ending position. The ending position represents the ending of the hole drilled by the drill bit in the bone 140. In FIG. 13, the ending position is a position 160 where the drill bit exits the far cortex 146. The processor of the device 10 determines the ending position as a position of the drill bit at a time of the electrical current dropping by a threshold amount. In one embodiment, the processor determines a maximum current as an average of a plurality of previous current measurements, and determines the ending position as a position of the drill bit at a time of the electrical current drops by a threshold amount from the maximum current. Referring to FIG. 13, the processor of the device 10 determines the electrical current 162 drops by the threshold amount, and determines the ending position as the position 160.

The drill bit is then automatically retracted in response to determining the ending position in order to minimize the possibility of drilling the hole too deep and injuring the patient.

In addition, once the starting position (the position 148) and the ending position (the position 160) are determined, the depth of a hole 164 drilled into the bone 140 is determined as a distance 166. The determined depth is used to select a screwdriver bit and screw to be used in block 132 discussed below. As a result, the possibility of the user inserting a screw with the wrong length in a subsequent implantation process may be minimized, and the amount of wasted hardware and total costs may be reduced. Further, the number of radiographs to verify the depth of the hole may be reduced; thus, avoid exposing the patient, surgeon, and staff to harmful radiation from the radiographs.

Returning to FIG. 12, in block 130, the drill bit is unloaded from the mount 96. In particular, the drill bit that was loaded into the mount 96 in block 124 is removed from the mount 96 and placed back into the drum 30. A bit is unloaded from the mount 96 by rotating the drum 30 until an empty chamber 40 is positioned lateral to the mount 96. Referring to FIG. 4, the table 34 is then moved rightward along the axis 62 by the table motor 36 until the chamber 40 is aligned in front of the mount 96 (the mounting position). The collet release actuator 100 then unloads the drill bit from the mount 96 to the drum 30. The table motor 36 returns the table 34 to the loading position.

In block 132, a screw holder 76, which includes a screwdriver bit and screw, is loaded into the mount 96. The screw holder 76 is selected from the drum 30 using the user interface 20, and is inserted into the mount 96, where the screw holder 76 is clamped. A screw holder 76 is loaded into the mount 96 by rotating the drum 30 until a chamber 40 with the screw holder 76 is positioned lateral to the mount 96. Referring to FIG. 4, the table 34 is then moved rightward along the axis 62 by the table motor 36 until the chamber 40 is aligned in front of the mount 96 (the mounting position). The collet release actuator 38 then unloads the screw holder 76 from the drum 30 to the mount 96. The table motor 36 returns the table 34 to the loading position.

In block 134, implantation process is performed. An implantation process is performed to screw the screw in the screw holder 76 loaded in block 132 into the hole drilled by the drill process in block 128. During the implantation process, the drive motor 98 rotates the mount 96, along with the screwdriver bit in the screw holder 76, around the axis 120. Concurrently, the sled 94 is moved to the forward position by rotating the lead screw 90 in a first direction with the lead screw motor 92. As discussed above, the sleeve 82 of the screw holder 76 is configured to securely hold the screw and release once the screw is fully inserted into the bone.

Once the screw is screwed into the hole to a desired depth, the screw holder 76 is retracted from the bone. The screw holder 76 is retracted by rotating the lead screw 90 in a second direction, opposite to the first direction, with the lead screw motor 92. In one embodiment, the device 10 is programmed to stop short of final tightening of the screw to allow the user to do final tightening by hand. In one embodiment, the depth of the screw is measured by, for example, the rotations of the lead screw motor 92, and displayed on the user interface 20. The depth of the hole may also be detected using various sensors, such as pressure and distance sensors.

It is noted that the device 10, itself, remains stationary with respect to the handle 16 during the implantation process, including the retraction of the screw holder 76. Further, the user does not apply physical force to push the device 10 to screw the screw into the bone. As a result, the user will not suffer from fatigue after inserting several screws.

The various embodiments described above provide a drill and implant device and method for using the same. The device is configured to automatically drill a hole into an object, such as a bone, stop once a desired depth has been reached, and subsequently insert an implant into the hole. The device is able to perform the drilling and the implantation without manually changing tools and without applying a physical force to the device. Further, the user may leave the device in a stationary position with respect to the handle 16 during the drilling and the implantation.

Although the various embodiments described above utilize the device 10 for surgical applications, the device 10 may be used for other applications as well. For example, the device 10 may be used for construction applications, home improvement applications, and various other types of applications.

A medical device, may be summarized as including: a handle; a body coupled to the handle; a tool changer in the body, the tool changer including: a table configured to move along a first axis; a drum coupled to the table, the drum configured to move with the table along the first axis and rotate around a second axis transverse to the first axis, the drum including a plurality of chambers configured to house a plurality of tools; and a first collet release actuator coupled to the table, the first collet release actuator configured to unload a tool of the plurality of tools from the drum; and a delivery device in the body and positioned lateral to the tool changer, the delivery device including: a frame; a lead screw coupled to the frame, the lead screw configured to rotate around a third axis; a sled coupled to the lead screw, the lead screw configured to move the sled along the third axis; a mount coupled to the sled, the mount configured to move with the sled along the third axis, the mount configured to hold the tool and rotate around a fourth axis; and a second collet release actuator coupled to the sled, the second collet release actuator configured to move with the sled along the third axis, the first collet release actuator configured to unload the tool from the mount.

The tool changer may be configured to remain stationary with respect to the handle while the sled moves along the third axis.

The tool changer may include: a drum motor coupled to the table, the drum motor configured to rotate the drum around the second axis; and a table motor coupled to the table, the table motor configured to move the table along the first axis.

The tool changer may include a loading tray configured to hold a tool being loaded into the drum.

The delivery device may include: a lead screw motor coupled to the frame, the lead screw motor configured to rotate the lead screw around the third axis; and a drive motor coupled to the sled, the drive motor configured to rotate the mount around the fourth axis.

The plurality of tools may include a drill bit, a screwdriver bit, an awl, and a pin.

The plurality of tools may include a screw holder including: a collet; a screwdriver bit coupled to the collet; a screw positioned in front of the screwdriver bit; and a sleeve that couples the screwdriver bit and the screw to each other.

The lead screw may include a plurality of threads, and the sled may include a threaded portion mated with the plurality of threads.

The plurality of chambers may include at least two chambers.

A device may be summarized as including: a tool changer including a drum configured to move along a first axis and rotate around a second axis transverse to the first axis, the drum including a plurality of chambers configured to house a drill bit and a screwdriver bit; and a delivery device positioned lateral to the tool changer, the delivery device including a sled and a mount coupled to the sled, the sled configured to move along a third axis, the mount configured to move with the sled along the third axis and rotate around a fourth axis parallel to the third axis, the tool changer configured to load the drill bit and the screwdriver bit from the drum to the mount.

The third axis and the fourth axis may be transverse to the first axis.

The tool changer may include: a table that supports the drum; a drum motor coupled to the table, the drum motor configured to rotate the drum around the second axis; and a table motor coupled to the table, the table motor configured to move the table along the first axis.

The delivery device may include a lead screw configured to rotate around a fifth axis, the lead screw may include a plurality of threads, and the sled may include a threaded portion mated with the plurality of threads.

The device may further include: a handle; and a body coupled to the handle and housing the tool changer and the delivery device.

The plurality of chambers may be configured to house a screw holder including: a collet; the screwdriver bit coupled to the collet; a screw positioned in front of the screwdriver bit; and a sleeve that couples the screwdriver bit and the screw to each other.

A method may be summarized as including: loading, by a tool changer of a medical device, a drill bit from a drum of the tool changer to a mount of a delivery device of the medical device, the loading of the drill bit including: positioning, by the tool changer, a first chamber of the drum laterally to the mount by rotating the drum, the first chamber holding the drill bit; and aligning, by the tool changer, the first chamber with the mount by moving the drum laterally; and drilling, by the delivery device, a hole in a target area using the drill bit, the drilling of the hole including: rotating, by the delivery device, the mount and the drill bit; moving, by the delivery device, the mount and the drill bit forward; and retracting, by the delivery device, the mount.

The method may further include: unloading, by the delivery device, the drill bit from the mount to the first chamber; loading, by the tool changer, a screwdriver bit from the drum to the mount, the loading of the screwdriver bit including: positioning, by the tool changer, a second chamber of the drum laterally to the mount by rotating the drum, the second chamber holding the screwdriver bit; and aligning, by the tool changer, the second chamber with the mount by moving the drum laterally; and screwing, by the delivery device, a screw into the hole using the screwdriver bit, the screwing of the screw including: rotating, by the delivery device, the mount and the screwdriver bit; moving, by the delivery device, the mount and the screwdriver bit forward; and retracting, by the delivery device, the mount.

The method may further include: measuring, by the medical device, a depth of the hole, the measuring of the depth of the hole including: measuring, while there is no load on the drill bit, a first electrical current of a motor configured to rotate the mount; measuring, while there is a load on the drill bit, a second electrical current of the motor; and determining a starting position of the hole based on the first electrical current and the second electrical current.

The measuring of the depth of the hole may include: measuring, concurrently with the drilling, a third electrical current of the motor; determining a current drop of the third electrical current; determining an ending position of the hole in response to determining the current drop; and measuring the depth based on the starting position and the ending position.

The medical device may remain stationary with respect to a handle of the medical device during the drilling.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
   loading, by a tool changer of a medical device, a drill bit from a drum of the tool changer to a mount of a delivery device of the medical device, the loading of the drill bit including:
      positioning, by the tool changer, a first chamber of the drum laterally to the mount by rotating the drum, the first chamber holding the drill bit; and
      aligning, by the tool changer, the first chamber with the mount by moving the drum laterally; and
   drilling, by the delivery device, a hole in a target area using the drill bit, the drilling of the hole including:
      rotating, by the delivery device, the mount and the drill bit;
      moving, by the delivery device, the mount and the drill bit forward; and
      retracting, by the delivery device, the mount.

2. The method of claim 1, further comprising:
   unloading, by the delivery device, the drill bit from the mount to the first chamber;
   loading, by the tool changer, a screwdriver bit from the drum to the mount, the loading of the screwdriver bit including:
      positioning, by the tool changer, a second chamber of the drum laterally to the mount by rotating the drum, the second chamber holding the screwdriver bit; and
      aligning, by the tool changer, the second chamber with the mount by moving the drum laterally; and
   screwing, by the delivery device, a screw into the hole using the screwdriver bit, the screwing of the screw including:
      rotating, by the delivery device, the mount and the screwdriver bit;
      moving, by the delivery device, the mount and the screwdriver bit forward; and
      retracting, by the delivery device, the mount.

3. The method of claim 1, further comprising:
   measuring, by the medical device, a depth of the hole, the measuring of the depth of the hole including:
      measuring, while there is no load on the drill bit, a first electrical current of a motor configured to rotate the mount;
      measuring, while there is a load on the drill bit, a second electrical current of the motor; and
      determining a starting position of the hole based on the first electrical current and the second electrical current.

4. The method of claim 3 wherein the measuring of the depth of the hole includes:
   measuring, concurrently with the drilling, a third electrical current of the motor;
   determining a current drop of the third electrical current;
   determining an ending position of the hole in response to determining the current drop; and
   measuring the depth based on the starting position and the ending position.

5. The method of claim 1 wherein the medical device remains stationary with respect to a handle of the medical device during the drilling.

6. A method, comprising:
   moving, by a tool changer, a drum along a first axis until a first chamber of the drum is aligned with a mount of a delivery device;
   loading, by the tool changer, a drill bit from the first chamber to the mount;
   moving, by the delivery device, the mount and the drill bit along a second axis transverse to the first axis; and
   rotating, by the delivery device, the mount and the drill bit concurrently with the moving of the mount and the drill bit along the second axis.

7. The method of claim 6, further comprising:
   retracting, by the delivery device, the mount along the second axis;
   unloading, by the delivery device, the drill bit from the mount to the first chamber;
   rotating, by the tool changer, the drum until a second chamber of the drum is lateral to the mount;
   moving, by the tool changer, the drum along the first axis until the second chamber is aligned with the mount;
   loading, by the tool changer, a screwdriver bit from the second chamber to the mount;
   moving, by the delivery device, the mount and the screwdriver bit along the second axis; and
   rotating, by the delivery device, the mount and the screwdriver bit concurrently with the moving of the mount and the screwdriver bit along the second axis.

8. The method of claim 6, further comprising:
   measuring, while there is no load on the drill bit, a first electrical current of a motor configured to rotate the mount;
   measuring, while there is a load on the drill bit, a second electrical current of the motor; and
   determining a starting position of a hole drilled by the drill bit based on the first electrical current and the second electrical current.

9. The method of claim 8, further comprising:
   measuring, concurrently with the rotating of the mount and the drill bit, a third electrical current of the motor;
   measuring, concurrently with the rotating of the mount and the drill bit, a fourth electrical current of the motor that is lower than the third electrical current; and
   determining an ending position of the hole based on the third electrical current and the fourth electrical current.

10. The method of claim 9, further comprising:
    determining a depth of the hole based on the starting position and the ending position.

11. The method of claim 6, further comprising:
    rotating, by the tool changer, the drum until the first chamber is lateral to the mount.

12. The method of claim 6 wherein a handle, which is coupled to the tool changer and the delivery device, remains stationary with respect to the tool changer and the delivery device during the rotating of the mount and the drill bit.

13. A method, comprising:
rotating a drum to a first position, a first chamber being positioned lateral to a mount in the first position;
aligning the first chamber with the mount by moving the drum in a first direction;
loading, subsequent to aligning the first chamber with the mount, a bit from the first chamber into the mount;
moving the bit in the mount in a second direction transverse to the first direction; and
rotating, concurrently with moving of the bit in the mount, the bit in the mount.

14. The method of claim 13 wherein the bit is a drill bit or a screwdriver bit.

15. The method of claim 13, further comprising:
moving, prior to moving of the bit in the mount, the drum in a third direction opposite to the first direction.

16. The method of claim 13, further comprising:
moving the bit in the mount in a third direction opposite to the second direction; and
unloading, subsequent to moving the bit in the mount in the third direction, the bit from the mount into the first chamber.

17. The method of claim 16, further comprising:
rotating the drum to a second position, a second chamber being positioned lateral to the mount in the second position;
aligning the second chamber with the mount by moving the drum in the first direction;
loading, subsequent to aligning the second chamber with the mount, another bit from the second chamber into the mount;
moving the another bit in the mount in the second direction; and
rotating, concurrently with moving of the another bit in the mount, the another bit in the mount.

18. The method of claim 13, further comprising:
measuring a first electrical current of a motor configured to rotate the bit in the mount;
measuring a second electrical current of the motor; and
determining a starting position of a hole formed by the bit based on the first electrical current and the second electrical current.

19. The method of claim 18, further comprising:
measuring a third electrical current of the motor;
measuring a fourth electrical current of the motor; and
determining an ending position of the hole based on the third electrical current and the fourth electrical current.

20. The method of claim 19, further comprising:
determining a depth of the hole based on the starting position and the ending position.

\* \* \* \* \*